United States Patent [19]

Meguro et al.

[11] Patent Number: 4,687,777
[45] Date of Patent: Aug. 18, 1987

[54] THIAZOLIDINEDIONE DERIVATIVES, USEFUL AS ANTIDIABETIC AGENTS

[75] Inventors: Kanji Meguro, Nishinomiya; Takeshi Fujita, Takarazuka, both of Japan

[73] Assignee: Takeda Chemical Industries, Ltd., Osaka, Japan

[21] Appl. No.: 820,390

[22] Filed: Jan. 17, 1986

[30] Foreign Application Priority Data

Jan. 19, 1985 [JP] Japan .................................. 60-8085

[51] Int. Cl.$^4$ ..................... A61K 31/44; C07D 417/04
[52] U.S. Cl. ..................................... 514/342; 546/280
[58] Field of Search ........................ 546/280; 514/342

[56] References Cited

U.S. PATENT DOCUMENTS 4,287,200 9/1981 Kawamatsu et al. ............... 424/270

OTHER PUBLICATIONS

March, J., Adv. Org. Chem., 2nd ed., pp. 806–807.
Sohda et al., Chem. Pharm. Bull. 30(10) 3563–3573, 3580–3600 (1982).
Fujita et al., Diabetes, vol. 32, 804–810 (1983).
Sohda et al., Chem. Pharm. Bull., 32(6) 2267–2278 (1984).

Primary Examiner—Henry R. Jiles
Assistant Examiner—J. Richter
Attorney, Agent, or Firm—Wenderoth, Lind & Ponack

[57] ABSTRACT

Thiazolidinedione derivatives of the formula:

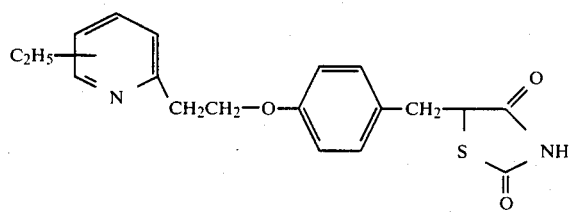

and pharmacologically acceptable salts thereof are novel compounds, which exhibit in mammals blood sugar- and lipid-lowering activity, and are of value as a therapeutic agent for treatment of diabetes and hyperlipemia.

5 Claims, No Drawings

THIAZOLIDINEDIONE DERIVATIVES, USEFUL AS ANTIDIABETIC AGENTS

This invention relates to novel thiazolidinedione derivatives, a method of preparing them and antidiabetic agents containing same, which are utilized in the field of medicines.

A variety of biguanide and sulfonylurea derivatives have been used clinically as antidiabetic agents.

However, the biguanides are now scarcely used, because they tend to cause lactic acidosis, and use of the sulfonylureas, though they have strong hypoglycemic activities, requires sufficient precaution, because they frequently cause serious hypoglycemia. Therefore, a new type of antidiabetic agent free from these defects has been desired.

On the other hand, in Japanese Unexamined Patent Publication Nos. 22636/1980 and 64586/1980, Chemical & Pharmaceutical Bulletin, 30, p. 3563 (1982), ibid, 30, p. 3580 (1982), and ibid, 32, p. 2267 (1984), reference is made to a variety of thiazolidinediones having blood glucose and lipid lowering actions. Antidiabetic activity of ciglitazone was also reported in Diabetes, 32, p. 804 (1983). Those compounds, however, have not yet been put to practical use. As the reasons, (1) insufficient activities or/and (2) serious toxicities may be mentioned.

The present inventors synthesized various compounds which are not concretely described in the above-mentioned publications of unexamined patent applications and have made studies on them to find the compounds exhibiting potent pharmacological effects with lower toxicity.

The present invention is to provide compounds which can be practically used as antidiabetic agents having a broad safety margin between pharmacological effect and toxicity or unfavorable side reactions.

The present invention relates to:
1. A compound of the formula:

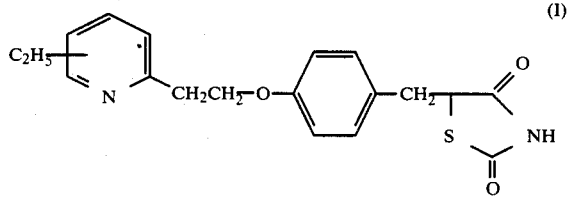

or a pharmacologically acceptable salt thereof, 2. an antidiabetic agent, which contains as the effective component a compound of the formula (I) or a pharmacologically acceptable salt thereof, and 3. a method of preparing a compound of the formula (I) or a pharmacologically acceptable salt thereof, which comprises hydrolyzing a compound of the formula:

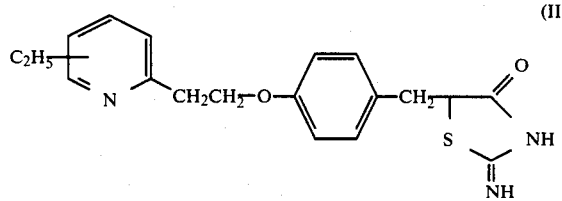

The compounds representable by the above formula (I) include, specific ones.
5-[4-[2-(3-ethyl-2-pyridyl)ethoxy]benzyl]-2,4-thiazolidinedione,
5-[4-[2-(4-ethyl-2-pyridyl)ethoxy]benzyl]-2,4-thiazolidinedione,
5-[4-[2-(5-ethyl-2-pyridyl)ethoxy]benzyl]-2,4-thiazolidinedione,
5-[4-[2-(6-ethyl-2-pyridyl)ethoxy]benzyl]-2,4-thiazolidinedione.

The compound (I) of this invention contains both basic nitrogen and acid nitrogen in its molecule, and it can be converted to a pharmacologically acceptable salt, when desired, by using a suitable acid or base.

Such acid salts are exemplified by mineral salts (e.g. hydrochloride, hydrobromide, sulfate, etc.), organic acid salts (e.g. succinate, maleate, fumarate, malate, tartrate, etc.) and sulfonates (e.g. methanesulfonate, benzenesulfonate, toluenesulfonate, etc.). Such basic salts are exemplified by alkali metal salts e.g. sodium salt, potassium salt, alkaline earth metal salts, e.g. calcium salt, etc. All of these salts can be prepared by per se known means.

The compound (I) of this invention or a pharmacologically acceptable salt thereof exhibits blood-glucose and blood-lipid lowering action with lower toxicity, and may be safely administered, orally or parenterally, as it is or advantageously as a pharmaceutical composition comprising an effective amount of the compound (I) or its pharmacologically acceptable salt and a pharmacologically acceptable carrier, excipient or diluent therefor, in the form of for example powder, granule, tablet, hard capsule, soft capsule, dry syrup, suppository, injection or the like.

The composition for oral administration such as powder, granule, tablet, hard capsule, soft capsule and dry syrup may be prepared by a per se known conventional manner, and may comprise carriers, excipients or diluents conventionally used in the pharmaceutical art. For example, suitable carriers or excipients include lactose, starch, sugar, magnesium stearate, etc. As the excipients in the preparation of soft capsules, there may be used nontoxic, pharmaceutically acceptable oils and fats of animal, vegetable or mineral origin. The essential active ingredients are generally dissolved in these oils and fats before filling soft capsules therewith.

The compositions for parenteral administration may, for example, be injections and suppositories. The injectable preparations may be prepared in the form of solutions or suspensions. Injectable preparations in the form of aqueous solutions may be prepared by a conventional manner. The suppositories for rectal administration can be prepared by incorporating the compound (I) or its pharmacologically acceptable salt with a conventional suppository base.

The pharmaceutical composition of the present application can be used as an antidiabetic agent for mammals including man.

Oral administration to an adult patient is 0.05–10 mg/kg body weight/day, preferably 0.5–5 mg/kg body weight/day, and parenterally 0.01–10 mg/kg body weight/day, preferably 0.1–1.0 mg/kg body weight/day once daily or divided into 2–4 times a week.

The compound represented by the above mentioned general formula (I) and pharmacologically acceptable salts thereof [hereinafter collectively referred to as "Compound (I)"] can be prepared by subjecting a compound represented by the general formula (II) to hydrolysis. This reaction proceeds advantageously in a proper solvent by employing a mineral acid. The solvent is exemplified by alcohols (e.g. methanol, ethanol, propanol, butanol, isobutanol, 2-methoxyethanol, etc.), dimethylsulfoxide, sulfolane, dioxane, tetrahydrofuran, dimethoxyethane, etc., and the mineral acid is exemplified by hydrochloric acid, hydrobromic acid, sulfuric acid, etc. The reaction temperature ranges from 20° C. to 150° C. The reaction time is 0.5–20 hours.

The compound (I) or a pharmacologically acceptable salt thereof produced as mentioned above can be isolated and purified by conventional means such as concentration, extraction, recrystallization, chromatography, etc.

The compound represented by the above-mentioned general formula (II) can be produced by the following reactions:

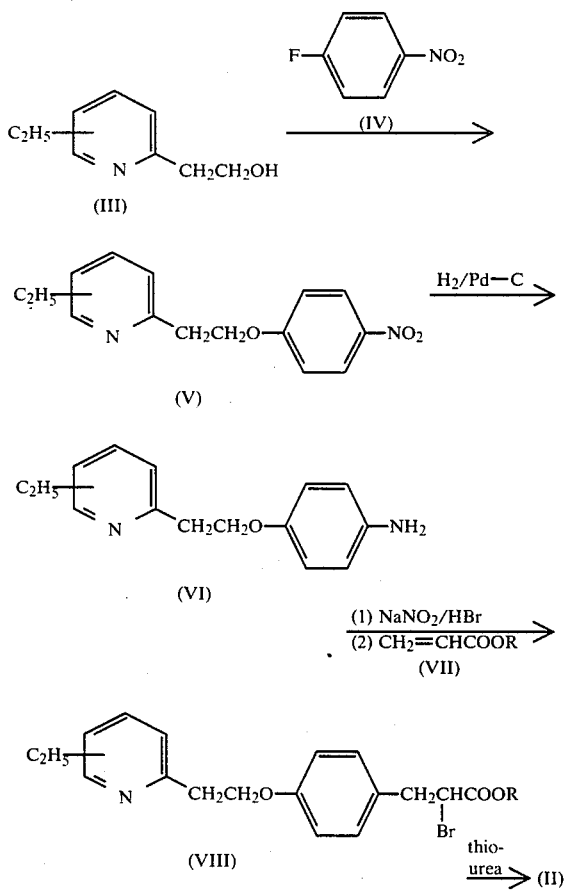

[wherein R stands for hydrogen or lower alkyl].

The lower alkyl group represented by R is exemplified by ($C_{1-4}$) alkyl such as methyl, ethyl, propyl, isopropyl and butyl.

The reaction for producing compound (V) from compound (III) and compound (IV) is conducted in the presence of, for example, sodium hydride. This reaction can be carried out in a solvent e.g. dimethylformamide and tetrahydrofuran at a temperature ranging from −10° C. to 30° C. The reaction from compound (V) to compound (VI) can easily be conducted by conventional catalytic reduction employing, for example, palladium-carbon as the catalyst. Compound (VI) may be isolated as the pure product or can be subjected to the subsequent reaction step without isolation and purification. Compound (VIII) can be produced by subjecting compound (VI) to diazotization in the presence of an aqueous solution of hydrobromic acid, then allowing the resultant to react with acrylic acid or its lower alkyl ester (VII) in the presence of a copper catalyst e.g. cuprous oxide, cupric oxide, cuprous chloride, cupric chloride, cuprous bromide, cupric bromide, etc. (Meerwein arylation). Compound (VIII) can be purified by e.g. chromatography, and subjected to the subsequent reaction without isolation or purification.

Compound (VIII) is then allowed to react with thiourea to give compound (II). This reaction is carried out usually in alcohols (e.g. methanol, ethanol, propanol, butanol, isobutanol, 2-methoxyethanol, etc.), dimethylsulfoxide, sulfolane, etc. The reaction temperature is usually 20°–180° C., preferably 60°–150° C. The amount of thiourea to be employed is 1–2 moles relative to one mole of compound (VIII).

In this reaction, as the reaction proceeds, hydrogen bromide is produced as the by-product, and, for capturing this by-product, the reaction may be conducted in the presence of sodium acetate, potassium acetate, etc., in an amount of usually 1–1.5 mole relative to 1 mole of compound (VIII). The resultant compound (II) can be isolated, but may be subjected to the hydrolysis step directly without isolation.

(I) of the present invention has an excellent blood glucose and lipid lowering activity and is remarkably low in toxicity, which is supported by the following experimental data.

EXPERIMENTAL EXAMPLES

1. Blood Glucose and Lipid Lowering Activity in Mice

To male KKA$^y$ mice (8–10 weeks old, 5 mice/group), the test compounds (at three dosage levels) were given as a dietary admixture in CE-2 powdered diet (CLEA Japan) with free access to water for 4 days.

Blood samples were taken from the orbital vein on the 5th day.

Blood glucose and plasma triglyceride (TG) were determined by a glucose oxidase method and by using a commercially available assay kit, Cleantech TG-S (Iatron, Japan), respectively. Based on dose-response curves for blood glucose and plasma TG lowering activity, effective dose of each test compound in 25% decrease from the control value was calculated as the value of ED25 (mg/kg/day) The results are shown in Table 1.

2. Lipid Lowering Activity in Rats

Male Sprague-Dawley rats (7 weeks old, 5 rats/group) were maintained on the laboratory chow (CE-2, CLEA, Japan) with free access to water. All the test compounds (at three dosage levels) suspended in 5% gum arabic solution were forcedly administered to the animals orally for 4 days. Blood samples were taken from the tail vein on the 5th day. Plasma TG was determined using a commercially available assay kit, Cleantech TG-S (Iatron). Based on dose-response curves for lipid lowering activity, effective dose of each test compound in 25% decrease from the control value was calculated as the value of $ED_{25}$ (mg/kg/day). The results are shown in Table 1.

3. Two-week Toxicity Study in Rats

Male and female Sprague-Dawley rats (5 weeks old, 5 rats/group) were maintained on the laboratory chow (CE-2, CLEA Japan) with free access to water. All the test compounds suspended in 5% gum arabic solution were forcedly administered orally to the animals for 2 weeks once daily. The dose was 100 mg/kg/day for every test compound. The animals were sacrificed in about 20 hours of fasting after termination of the two-week administration by withdrawing blood samples from the abdominal aorta using heparinized syringes under ether anesthesia. Liver and heart were removed and weighed. Hematology analysis was also carried out using an automatic cell counter. The data represent % increase or decrease from the control value (non-drug treated) as shown in Table 1.

in Table 1, Compound (I) of this invention is superior to the compounds (a), (c), (d) and (e) and comparable to the compound (b) in hypoglycemic and hypolipidemic activities, while showing extremely low toxicity as compared with the compounds (a), (b), (d) and (e). Such an effect as above caused by the introduction of an ethyl group is quite unexpected. Thus, compound (I) of the present invention exhibits excellent hypoglycemic and hypolipidemic activities, and little toxicity to internal organs and blood even by continuous administration for a long period of time. Therefore, compound (I) is of value as a therapeutic agent for Type II diabetes accompanied by obesity or hyperlipemia in mammals including man.

TABLE 1

$$A-O-\langle\text{phenyl}\rangle-CH_2-\underset{S}{\overset{O}{\underset{\underset{O}{\|}}{\overset{\|}{\text{C}}}}}\text{NH}$$

| Compound A | Blood Glucose $(ED_{25})$ mouse | $TG(ED_{25})$ mouse | rat | Two-weeks toxicity (rat, %) | | | | | |
|---|---|---|---|---|---|---|---|---|---|
| | | | | Liver weight | | Heart weight | | number of erythrocyte | |
| | | | | ♂ | ♀ | ♂ | ♀ | ♂ | ♀ |
| (I) $C_2H_5$-pyridyl-$CH_2CH_2$— | 6 | 6 | 3 | −0.7 | −3.5 | +0.9 | −3.9 | −3.4 | −0.7 |
| (a) cyclohexyl-$CH_3$-$CH_2$— (ciglitazone) | 40 | 40 | 70 | +6.6* | +10.8* | +13.4* | +4.0 | +3.5 | −0.2 |
| (b) $CH_3$-pyridyl-$CH_3$-$CH_2CH_2$— | 4 | 3 | 5 | +3.8 | +10.7** | +19.9** | +17.8** | −2.9 | −8.8** |
| (c) $CH_3$-pyridyl-$CH_2CH_2$— | 20 | 20 | — | +1.3 | −1.2 | +7.2 | +3.0 | −4.2 | −6.0 |
| (d) $CH_3$-pyridyl-$CH_2CH_2$— | 20 | 20 | — | +8.8* | +8.4** | +3.3 | +7.3* | −3.7 | −2.5 |
| (e) $CH_3$-pyridyl-$CH_2CH_2$— | 20 | 20 | — | −2.3 | +6.6** | +10.9 | +9.8* | −8.7* | −7.0** | t-test: *P < 0.05; **P < 0.01

In Table 1, Compound (I) is a compound under the coverage of the present invention, compounds (a) and (b) are known compounds concretely referred to in the Japanese unexamined Patent Publication No. 22636/1980.

While compounds (c), (d) and (e) are not concretely referred to in the above-mentioned patent publication, they are cited for comparison, since they are similar to compound (I) of this invention in their chemical structures. As is apparent from the experimental results given

EXAMPLE 1

(a) To a solution of 2-(5-ethyl-2-pyridyl)ethanol (53.0 g) and 4-fluoronitrobenzene (47.0 g) in DMF (500 ml) was added portionwise under ice-cooling 60% sodium hydride in oil (16.0 g). The mixture was stirred under ice-cooling for one hour, then at room temperature for 30 minutes, poured into water and extracted with ether.

The ether layer was washed with water and dried (MgSO$_4$). The solvent was evaporated off to give 4-[2-(5-ethyl-2-pyridyl)ethoxy]nitrobenzene as crystals (62.0 g, 62.9%). Recrystallization from ether-hexane gave colorless prisms, m.p. 53°–54° C.

(b) A solution of 4-[2-(5-ethyl-2-pyridyl)ethoxy]nitrobenzene (60.0 g) in methanol (500 ml) was hydrogenated at room temperature under one atmospheric pressure in the presence of 10% Pd-C (50% wet, 6.0 g). The catalyst was removed by filtration and the filtrate was concentrated under reduced pressure. The residual oil was dissolved in acetone (500 ml)-methanol (200 ml). To the solution was added a 47% HBr aqueous solution (152 g). The mixture was cooled, to which was added dropwise a solution of NaNO$_2$ (17.3 g) in water (30 ml) at a temperature not higher than 5° C. The whole mixture was stirred at 5° C. for 20 minutes, then methyl acrylate (112 g) was added thereto and the temperature was raised to 38° C. Cuprous oxide (2.0 g) was added to the mixture in small portions with vigorous stirring. The reaction mixture was stirred until nitrogen gas evolution ceased, and was concentrated under reduced pressure. The concentrate was made alkaline with concentrated aqueous ammonia, and extracted with ethyl acetate. The ethyl acetate layer was washed with water and dried (MgSO$_4$) The solvent was evaporated off to leave methyl 2-bromo-3-{4-[2-(5-ethyl-2pyridyl)ethoxy]phenyl}propionate as a crude oil (74.09 g, 85.7%). IR(neat)cm$^{-1}$1735. NMR $\delta$(ppm) in CDCl$_3$: 1.21 (3H, t, J=7), 2.60 (2H, q, J=7), 3.0–3.6 (4H, m), 3.66 (3H, s), 4.30 (2H, t, J=7), 4.3 (1H, m), 6.7–7.5 (6H, m), 8.35 (1H, d, J=2).

(c) A mixture of the crude oil of methyl 2-bromo-3-{4-[2-(5-ethyl-2-pyridyl)ethoxy]phenyl}propionate (73.0 g) obtained in (b) thiourea (14.2 g), sodium acetate (15.3 g) and ethanol (500 ml) was stirred for 3 hours under reflux. The reaction mixture was concentrated under reduced pressure, and the concentrate wasneutralized with a saturated aqueous solution of sodium hydrogencarbonate, to which were added water (200 ml) and ether (100 ml). The whole mixture was stirred for 10 minutes to yield 5-{4-[2-(5-ethyl-2-pyridyl)ethoxy]benzyl}-2-imino-4-thiazolidinone as crystals (0.3 g, 523.0%). Recrystallization from methanol gave colorless prisms, m.p. 187°–188° C. (decomp.). Elemental analysis for C$_{19}$H$_{21}$N$_3$O$_2$S Calcd.: C, 64.20; H, 5.95; N, 11.82. Found: C, 64.20; H, 5.84; N, 11.73.

(d) A solution of 5-{4-[2-(5-ethyl-2-pyridyl)ethoxy]benzyl}-2-imino-4-thiazolidinone (23.5 g) in 2N HCl (200 ml) was refluxed for 6 hours. The solvent was evaporated off under reduced pressure, and the residue was neutralized with a saturated aqueous solution of sodium hydrogencarbonate. The crystals (23.5 g, 97.5%) which precipitated were collected by filtration and recrystallized from DMF-H$_2$O to give 5-{4-[2-(5-ethyl-2-pyridyl)ethoxy]benzyl}-2,4-thiazolidinedione as colorless needles (20.5 g, 86.9%), m.p. 183°–184° C.

Elemental Analysis for C$_{19}$H$_{20}$N$_2$O$_3$S Calcd: C, 64.02; H, 5.66; N, 7.86. Found: C, 63.70; H, 5.88; N, 8.01.

(e) To a suspension of 5-{4-[2-(5-ethyl-2-pyridyl)ethoxy]benzyl}-2,4-thiazolidinedione (356 mg) in methanol (10 ml) was added 28% sodium methylate/methanol solution (0.2 g) to make a solution. This solution was concentrated and diluted with ethyl ether to yield crystals. The crystals were collected by filtration and recrystallized from methanol-ethanol to give the sodium salt of 5-{4-[2-(5-ethyl-2-pyridyl)ethoxy]benzyl}-2,4-thiazolidinedione as colorless crystals (298 mg, 78.8%), m.p. 262°–263° C. (decomp.).

Elemental analysis for C$_{19}$H$_{19}$N$_2$O$_3$SNa:
Calcd.: C, 60.31; H, 5.06; N, 7.40.
Found: C, 60.20; H, 5.07; N, 7.52.

EXAMPLE 2

| | | |
|---|---|---|
| (1) | 5-{4-[2-(5-ethyl-2-pyridyl)ethoxy] benzyl}-2,4-thiazolidinedione | 100 g |
| (2) | Lactose | 50 g |
| (3) | Corn starch | 15 g |
| (4) | Carboxymethyl cellulose calcium | 44 g |
| (5) | Magnesium stearate | 1 g |
| | | 210 g |

The whole amounts of (1), (2) and (3) and 30 g of (4) were kneaded with water and dried in vacuo, followed by granulation. With the resultant granules were mixed 14 g of (4) and 1 g of (5) and the whole mixture was tableted with a tableting machine to give 1000 tablets 8 mm in diameter and each containing 100 mg of (1).

REFERENCE EXAMPLE 1

The compounds listed in Table 2 were prepared in accordance with Example 1-(a).

TABLE 2

| R | mp | Recrystallization solvent | yield |
|---|---|---|---|
| 3-CH$_3$ | 116–117° C. | ethyl acetate-hexane | 62.9% |
| 4-CH$_3$ | 73–74° C. | ethyl acetate-hexane | 57.3% |
| 5-CH$_3$ | 97–98° C. | ethyl acetate-hexane | 72.3% |

REFERENCE EXAMPLE 2

In accordance with Example 1-(b), the following compounds were prepared.

Methyl 2-bromo-3-{4-[2-(3-methyl-2-pyridyl)ethoxy]phenyl}propionate; IR(Neat)cm$^{-1}$: 1735. NMR $\delta$ (ppm) in CDCl$_3$: 2.34 (3H, s), 3.10 (1H, dd, J=14 and 7), 3.25 (2H, t, J=6), 3.38 (1H, dd, J=14 and 7), 3.67 (3H, s), 4.29 (1H, t, J=7), 4.37 (2H, t, J=6), 6.8–7.5 (6H, m), 8.35 (1H, dd, J=5 and 2).

2-Bromo-3-{4-[2-(4-methyl-2-pyridyl)ethoxy]phenyl}propionic acid methyl ester; IR(Neat)cm$^{-}$1735. NMR $\delta$ (ppm) in CDCl$_3$: 2.30 (3H, s), 3.10 (1H, dd, J=14 and 7), 3.26 (3H, t, J=7), 3.37 (1H, dd, J=14 and 7), 3.67 (3H, s), 4.30 (3H, t, J=7), 6.7–7.36(6H, m), 8.37 (1H, d, J=6)

REFERENCE EXAMPLE 3

A solution of 4-[2-(5-methyl-2-pyridyl)ethoxy]nitrobenzene (15.0 g) in methanol (150 ml) was subjected to catalytic reduction under 1 atmospheric pressure in the presence of 10% Pd-C (50% wet, 2.0 g). The catalyst was filtered off, and the filtrate was concentrated to give 4-[2-(5-methyl-2-pyridyl)ethoxy]aniline as crystals (12.3 g, 92.5%). Recrystallization from ethyl acetate-hexane gave colorless prisms, m.p. 74°–75° C.

Elemental analysis for C$_{14}$H$_{16}$N$_2$O: Calcd.: C, 73.66; H, 7.06; N, 12.27. Found: C, 73.84; H, 7.17; N, 12.06.

REFERENCE EXAMPLE 4

To a mixture of 4-[2-(5-methyl-2-pyridyl)ethoxy]aniline (12.0 g), 47% aqueous HBr solution (36.5 g) and methanol (40 ml)-acetone (80 ml) was added dropwise a solution of NaNO$_2$ (4.0 g) in water (10 ml) at 5° C. or below. The whole mixture was stirred at 5° C. for 20 minutes, then methyl acrylate (27.0 g) was added thereto and the temperature was raised to 38° C. Cuprous oxide (1.0 g) was added to the mixture in small portions with vigorous stirring. After nitrogen gas evolution had ceased, the reaction mixture was concentrated under reduced pressure. The concentrate was made alkaline with concentrated aqueous ammonia and extracted with ethyl acetate. The ethyl acetate layer was washed with water and dried (MgSO$_4$). The solvent was evaporated off to leave methyl 2-bromo-3-{4-[2-(5-methyl-2-pyridyl)ethoxy]phenyl}-propionate as a crude oil (17.5 g, 87.5%). IR(Neat)cm$^{-1}$: 1735. NMR δ (ppm) in CDCl$_3$: 2.27 (3H, s), 3.10 (1H, dd, J=14 and 7), 3.22 (2H, t, J=6), 3.38 (1H, dd, J=14 and 7), 3.66 (3H, s), 4.29 (2H, t, J=6), 4.32 (1H, t, J=7), 6.7–7.5 (6H, m), 8.34 (1H, d, J=2).

REFERENCE EXAMPLE 5

The compounds listed in Table 3 were prepared in accordance with Example 1-(c).

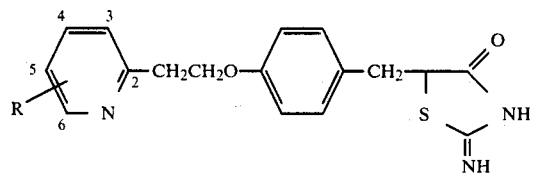

| R | mp (decomp.) | Recrystallization solvent | yield |
| --- | --- | --- | --- |
| 3-CH$_3$ | 230–231° C. | chloroform-methanol | 75.5% |
| 4-CH$_3$ | 190–191° C. | methanol | 48.0% |
| 5-CH$_3$ | 203–204° C. | chloroform-methanol | 58.2% |

REFERENCE EXAMPLE 6

The compounds listed in Table 4 were prepared in accordance with Example 1-(d).

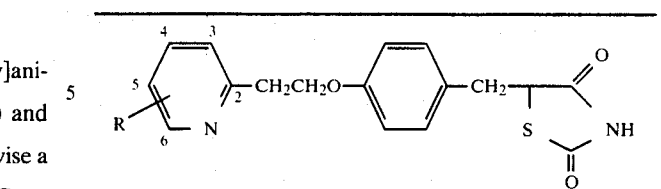

| R | mp | Recrystallization solvent | yield |
| --- | --- | --- | --- |
| 3-CH$_3$ | 210–211° C. | DMF-water | 65.7% |
| 4-CH$_3$ | 178–179° C. | chloroform-methanol | 75.3% |

REFERENCE EXAMPLE 7

A mixture of 2-imino-5-{4-[2-(5-methyl-2-pyridyl)ethoxy]benzyl}-4-thiazolidinone (8.0 g), 2N HCl (80 ml) and ethanol (80 ml) was refluxed for 16 hours. The reaction solution was neutralized with a saturated aqueous solution of sodium hydrogencarbonate to yield crystals. The crystals were collected by filtration and recrystallized from ethanol to give 5-{4-[2-(5-methyl-2pyridyl)ethoxy]benzyl}-2,4-thiazolidinedione as colorless prisms (7.0 g, 87.5%), m.p. 192°–193° C.

Elemental Analysis for C$_{18}$H$_{18}$N$_2$O$_3$: Calcd.: C, 63.14: H, 5.30; N, 8.18. Found: C, 63.22; H, 5.40: N, 8.11.

We claim:

1. A compound of the formula:

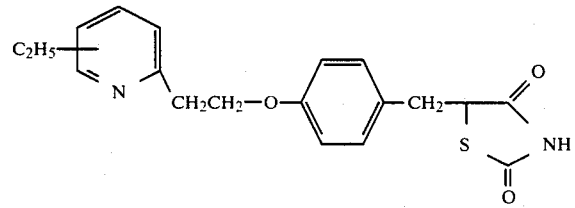

or a pharmacologically acceptable salt thereof.

2. A compound as claimed in claim 1, wherein the compound is 5-{4-[2-(5-ethyl-2-pyridyl)ethoxy]benzyl}-2,4-thiazolidinedione.

3. A compound as claimed in claim 1, wherein the compound is sodium salt of 5-{4-[2-(5-ethyl-2-pyridyl)ethoxy]benzylbenzyl}-2,4-thiazolidinedione.

4. A compound as claimed in claim 1, wherein the compound is 5-{4-[2-(6-ethyl-2-pyridyl)ethoxy]benzyl}-2,4-thiazolidinedione.

5. An antidiabetic composition which consists essentially of a compound of the formula:

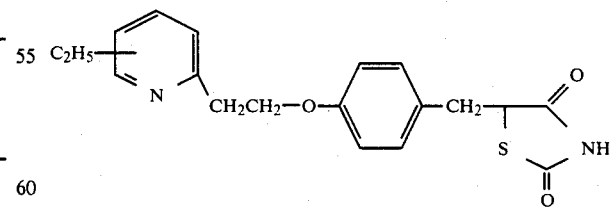

or a pharmacologically acceptable salt thereof, in association with a pharmacologically acceptable carrier, excipient or diluent.